(12) United States Patent
Kruse et al.

(10) Patent No.: US 10,429,265 B2
(45) Date of Patent: Oct. 1, 2019

(54) COMPONENT DEVICE AND METHOD FOR DETECTING A DAMAGE IN A BONDING OF A COMPONENT DEVICE

(71) Applicants: Airbus Defence and Space GmbH, Taufkirchen (DE); Airbus Operations GmbH, Hamburg (DE)

(72) Inventors: Thomas Kruse, Hamburg (DE); Thomas Körwien, Höhenkirchen (DE); Alois Friedberger, Oberpframmern (DE); Andreas Helwig, München (DE)

(73) Assignees: AIRBUS DEFENCE AND SPACE GMBH, Taufkirchen (DE); AIRBUS OPERATIONS GMBH, Hamburg (DE)

( * ) Notice: Subject to any disclaimer, the term of this patent is extended or adjusted under 35 U.S.C. 154(b) by 313 days.

(21) Appl. No.: 15/386,269

(22) Filed: Dec. 21, 2016

(65) Prior Publication Data

US 2017/0176282 A1 Jun. 22, 2017

(30) Foreign Application Priority Data

Dec. 22, 2015 (DE) .................. 10 2015 122 594

(51) Int. Cl.
*G01M 3/26* (2006.01)
*G01M 3/04* (2006.01)
(Continued)

(52) U.S. Cl.
CPC .............. *G01M 3/26* (2013.01); *B29C 65/48* (2013.01); *B29C 65/8246* (2013.01);
(Continued)

(58) Field of Classification Search
CPC .................................................. G01L 9/0054
(Continued)

(56) References Cited

U.S. PATENT DOCUMENTS 4,205,551 A * 6/1980 Clifford .............. G01M 3/2869
73/49.2
6,305,427 B1 * 10/2001 Priest, II ................. F16L 11/12
138/104
(Continued)

FOREIGN PATENT DOCUMENTS

DE 1934798 A1 6/1971
DE 3201515 A1 7/1983
(Continued)

OTHER PUBLICATIONS

Eurpean Patent Office, European Search Report for European Patent Application No. 16204811.0 dated May 19, 2017.
(Continued)

*Primary Examiner* — Eric S. McCall
*Assistant Examiner* — Timothy P Graves
(74) *Attorney, Agent, or Firm* — Lorenz & Kopf LLP (57) ABSTRACT

The disclosure relates to a component device, in particular for a primary supporting component of an aircraft, the component device having a first component element, a second component element, a bonding providing a connection between the first component element and the second component element, and a detector device having at least one interior space sensor device configured to measure a change in a pressure and/or a concentration of a gas surrounding the interior space sensor device. The first component element, the second component element, and the bonding confine an interior space. The interior space sensor device is arranged in the interior space.

10 Claims, 2 Drawing Sheets

(51) Int. Cl.
*G01N 19/08* (2006.01)
*B29C 65/48* (2006.01)
*B29C 65/82* (2006.01)
*B29C 65/00* (2006.01)
*G01M 3/32* (2006.01)
*G01N 3/12* (2006.01)
*G01N 19/04* (2006.01)
*B64C 1/12* (2006.01)
*B64C 3/26* (2006.01)
*B64D 45/00* (2006.01)
*B29C 65/52* (2006.01)

(52) U.S. Cl.
CPC ........ *B29C 66/1122* (2013.01); *B29C 66/131* (2013.01); *B29C 66/474* (2013.01); *B29C 66/721* (2013.01); *B29C 66/7394* (2013.01); *B64C 1/12* (2013.01); *B64C 3/26* (2013.01); *B64D 45/00* (2013.01); *G01M 3/04* (2013.01); *G01M 3/3272* (2013.01); *G01N 3/12* (2013.01); *G01N 19/04* (2013.01); *G01N 19/08* (2013.01); *B29C 65/52* (2013.01); *B29C 65/522* (2013.01); *B29C 65/526* (2013.01); *B29C 66/026* (2013.01); *B29C 66/71* (2013.01); *B29C 66/73753* (2013.01); *B29C 66/73754* (2013.01); *B29C 66/73755* (2013.01); *B29C 66/73756* (2013.01); *B29C 66/742* (2013.01); *B64D 2045/0085* (2013.01)

(58) Field of Classification Search
USPC .......................................... 73/40.7, 37, 49.2
See application file for complete search history.

(56) References Cited

U.S. PATENT DOCUMENTS

| | | |
|---|---|---|
| 2002/0029614 A1 | 3/2002 | Davey |
| 2004/0173006 A1* | 9/2004 | McCoy ................. G01M 3/225 73/40.7 |
| 2005/0042141 A1* | 2/2005 | Otani ..................... G01N 27/16 422/98 |
| 2009/0243128 A1* | 10/2009 | Nelson ............... B29C 43/3642 264/40.1 |
| 2017/0176062 A1* | 6/2017 | Qazi ...................... F25B 21/04 |

FOREIGN PATENT DOCUMENTS

| | | |
|---|---|---|
| DE | 20213973 U1 | 11/2002 |
| DE | 202013002157 U1 | 6/2014 |
| DE | 102013223019 A1 | 5/2015 |
| EP | 2431156 A1 | 3/2012 |
| JP | H10286885 A | 10/1998 |
| JP | 2000186973 A | 7/2000 |
| WO | 2012141779 A1 | 10/2012 |

OTHER PUBLICATIONS

German Patent and Trade Mark Office, Office Action in German Patent Application No. 10 2015 122 594.8 dated Sep. 22, 2016.

* cited by examiner

COMPONENT DEVICE AND METHOD FOR DETECTING A DAMAGE IN A BONDING OF A COMPONENT DEVICE

CROSS-REFERENCE TO RELATED APPLICATION

This application claims priority to German Patent Application No. 10 2015 122 594.8, filed Dec. 22, 2015, which is incorporated herein by reference in its entirety.

TECHNICAL FIELD

The present disclosure relates to a component device, in particular for a primary supporting component of an aircraft. The component device comprises a first component element, a second component element, and a bonding which provides a connection between the first component element and the second component element. The present disclosure further relates to a method which comprises the step: providing a component device which comprises two component elements being connected by the bonding and an interior space being fluidically connected to the bonding, which interior space is hermetically sealed for at least one type of gas.

BACKGROUND

Adhesive bindings for composite components are presently not certified for being used as exclusive joining element in primary supporting components of an aircraft. The main reason for that is that the adhesive bonding greatly depends on manufacturing parameters like impurity or surface preparation. All these influencing parameters may result in a weakened bonding or in debindering of the adhesive bonding. As to avoid this, preventing propagation of cracks is presently attempted. Alternatively, it is attempted to prevent cracks from growing.

As secondary adhesive bindings shall be used in composite components for primary supporting components, it is favorable that possible damages (debindering) can be found by persons without any specific knowledge within few flight cycles or during regular maintenance work. So far, providing sensors in the various connections is necessary for any monitoring of the state of structures (structural health monitoring). This results in complicated architectures, so that the advantages of composite connections, namely their light weight, cost-effectiveness, and durability are reduced.

For example, EP 2 431 156 A1 discloses using magnetostrictive parts in the connection to be monitored, wherein strains in the magnetostrictive parts caused by damages in the connection can be detected by an external sensor.

WO 2012/141779 A1 discloses a connection in which a fabric and an electric network with sensors are included which serve for monitoring the state of the connection.

SUMMARY

There may be a need to provide a simplified state monitoring for adhesive connections.

An aspect relates to a component device, in particular for a primary supporting component of an aircraft. The component device comprises a first component element, a second component element, a bonding, and a detector device. The bonding provides a connection between the first component element and the second component element. The detector device comprises at least one interior space sensor device which is adapted to measure a change of the pressure and/or of a concentration of a gas surrounding the interior space sensor device. The first component element, the second component element, and the bonding confine an interior space, wherein the interior space sensor device is arranged in the interior space.

In particular, the component device is a bonded composite of two components or component elements. In addition to the first component element and the second component element, the component device may comprise additional component elements which are connected with each other by a second, third, or by an additional bonding.

Preferably, the first component element comprises a first contact surface, while the second component element particularly comprises a second contact surface. Preferably, the bonding is provided between the first contact surface and the second contact surface. Preferably, the bonding establishes a (secondary) adhesive connection between the components. The adhesion may also be referred to as bonding and comprises the materials known from the prior art. In particular, the bonding is fluidically connected to (is in fluid communication with) the surrounding air at one of its outer surfaces, preferably a lateral surface. Preferably, the surrounding air is in direct contact with the bonding. For example, the bonding is arranged such that a first lateral margin of the bonding is fluidically connected to the interior space and/or a second lateral margin is fluidically connected to the surrounding of the component device.

In particular, the first component element is a stringer or a purlin which may be an angle profile to the additional and locally limited stiffening of fuselage panel tongues, wherein the angle profile preferably contributes to forming the interior space. In particular, the second component element is a part of the outer skin of the aircraft.

Preferably, the first component element is an omega stringer which comprises a first edge region and a second edge region which are arranged in one plane. The first edge region and the second edge region are connected with a bridge-like middle region so that a half space is confined by the first edge region, the middle region, and the second edge region. In particular, this half space is confined by the second component element, so that an interior space is confined by the first component element and by the second component element. Preferably, the first contact surface is provided at the first edge region and/or the second contact surface is provided at the second edge region at the same side where the half space is provided and where the bonding is arranged. The first component element is adhesively mounted to the second component element by the bonding. In particular, the second component element is provided in the form of a panel.

In particular, the first component element, the second component element, and the bonding are made of a gas-tight material, so that the interior space is hermetically sealed from an environment surrounding the component device. For this purpose, the first component element and/or the second component element comprises a closing device at the end faces of the component device, which closing device hermetically or gas-tightly seals the interior space of the component device from the environment or surroundings. Alternatively, the first component element and the second component element may be ring-shaped so that no end faces exist.

The following material combinations may be provided for the first component element and for the second component element: a cured composite component with another cured composite component; a cured composite component with an uncured composite component (with or without additional bonding, wherein the bonding is achieved by curing the up to now uncured composite component); a cured composite component with a metallic component; a cured composite component with a fiber metal laminate component (fiber metal laminate part); a cured composite component with a partially cured composite component (with or without additional bonding); a partially cured composite component with another partially cured composite component (with or without additional bonding) and any material combination in which at least one component comprises a resin, preferably a cyanate ester resin.

For applying the bonding, the first component and the second component, in particular the first contact surface and the second contact surface are preferably pretreated according to one of the following principles: global application of a chemical etching bath; local application by spraying; local application by vacuum application; local application onto the carrier material (including protection against contamination during transport); local application during a coating process by a brush; any other defined standard application method for fluids.

Preferably, a surface treatment is provided for treating the contact surfaces. Preferably, the contact surfaces undergo laser treatment and/or plasma treatment.

The bonding of the first component and the second component may be accomplished manually or in an automated process. The activation of the surface treatment is preferably stable for one year which gives the manufacturer the opportunity to provide manufacturing of bindings or tool concepts which enable a repeatable binding process without time constrictions or delay.

The interior space sensor device is provided in the interior space as to measure the pressure and/or the concentration of the gas being present in the interior space. In particular, the detector device, preferably the interior space sensor device, is connected with a control arrangement by means of which the measurement values determined by the detector device may be further processed. The connection between the detector device and the control arrangement may be accomplished in a wireless manner or by means of installed lines.

Preferably, the control arrangement comprises a microprocessor or is connected to a computer system, in particular of the aircraft. In particular, the control arrangement is adapted to output a message or an alarm if the detector device detects that the pressure and/or the concentration of the gas being present in the interior space changes by a certain predetermined amount.

Preferably, the interior space sensor device is attached to the first component element and/or to the second component element. In particular, the interior space sensor device comprises a gas sensor, for example a sensor on the basis of semiconducting metal oxide which may determine the concentration of a gas in the interior space. Furthermore, the interior space sensor device may be adapted as a pressure sensor which may determine the gas pressure in the interior space.

In case of a damage in the bonding, a gas exchange takes place between the interior space and the surroundings of the component device. Hence, the pressure or the concentration of the gas being present in the interior space may vary. The change in pressure may take place in several different ways. Firstly, during manufacturing of the component device a certain positive or negative pressure may be provided in the interior space which pressure may vary due to leakage caused by a damage in the bonding.

Alternatively, the pressure or the concentration of the gas in the interior space may vary as a result of changes of the pressure or of the concentration of the gas in the surroundings of the component device. For example, this may occur if the component device is provided in an aircraft so that the pressure or the gas concentration in the aircraft varies during flight. Changes of pressure or changes of concentration are not transferred to the interior space in case of intact bonding. Consequently, a relatively constant pressure and a rather varying gas concentration are measured in the interior space. A change in pressure and/or a change in gas concentration, in particular about a certain threshold value, indicates a damage in the bonding.

The gradient of the change in pressure and/or of the change in concentration in the interior space and/or in the outer space may be used to determine that a damage of the bonding exists. A change of the gradient of the change in pressure and/or of the change in concentration indicates that the gas exchange between the interior space and the outer space has varied.

Providing a threshold value for the change in pressure or the change in concentration which provokes outputting an alarm or a message when exceeded may make sense, for example, if the pressure in the interior space may vary due to temperature changes. In this manner, incorrect damage determination may be avoided.

The pressure and concentration values determined by the interior space sensor device are preferably monitored (observed) by the control arrangement. The control arrangement may generate an alarm signal or a notification in case a change is determined which indicates a damage in the bonding.

It is preferred that the detector device comprises an outer space sensor device which is adapted to measure a change of the pressure and/or of the concentration of a gas surrounding the outer space sensor device, wherein the outer space sensor device is arranged out of the interior space.

The outer space sensor device may be arranged at the first component element or at the second component element. However, it is also possible to arrange the outer space sensor device adjacent to the first component element and the second component element, for example at a wall of a space of an aircraft in which that first component element and the second component element are provided.

The outer space sensor device may be adapted analogue to the interior space sensor device. In particular, the outer space sensor device may comprise a gas sensor for detecting the concentration of a gas in the surroundings of the first and second component element and/or a pressure sensor for determining the pressure of the gas in the surroundings of the first component element and of the second component element. The outer space sensor device may be likewise connected with the control arrangement.

By means of the outer space sensor device and the interior space sensor device it is possible to monitor the course of the pressure and/or of the concentration of the gas in the interior space and outside the interior space. If the course of the pressure and/or of the concentration within the interior space correlates with that one outside the interior space, this indicates that a gas connection exists between the interior space and the outer space. The gas connection in turn indicates that a damage in the bonding is present.

Providing the outer space sensor device and the thereby possible determination of the correlation of the pressures and of the concentration of the gas makes it possible to neglect fluctuations in pressure in the interior space which are caused by temperature fluctuations or the like, or fluctuations in concentration which may result from absorption or emission of gases in the interior space. Thus, false positive notifications or alarms with regard to a damage at the bonding may be reduced.

It is preferred that the interior space sensor device comprises a first interior space sensor which is adapted to measure the absolute pressure of the gases surrounding the interior space sensor, and/or a second interior space sensor which is adapted to measure the partial pressure of a gas surrounding the interior space sensor, and/or a third interior space sensor which is adapted to measure the concentration of a gas surrounding the third interior space sensor, wherein preferably multiple first interior space sensors and/or multiple second interior space sensors and/or multiple third interior space sensors are provided in the interior space.

In particular, the first interior space sensor is adapted to measure the total pressure of all different gases which are present in the interior space. The first interior space sensor may be configured like a pressure sensor or barometer known in the prior art. The absolute pressure of the gas surrounding the first and the second component element typically differs at ground level and at flight level. Hence, changes in the absolute pressure in the interior space indicates that a gas connection exists between the interior space and the outer space, which is an evidence of a damage in the bonding, as explained above.

In particular, the second interior space sensor is adapted to measure a partial pressure of a gas being present in the interior space. Sensors for determining the partial pressure of gases are known from the prior art. For example, the second interior space sensor may determine the partial pressure of oxygen, ozone, or water vapor. Preferably, these gases are determined by means of the second interior space sensor as their partial pressures at ground level and at flight level of the aircraft differ so that, in case of a damage in the bonding, it is to be expected that the partial pressures of these gases change in the interior space.

In particular, the third interior space sensor may determine the concentration of water vapor, oxygen, or ozone. As explained above, the concentration of these gases changes at flight level of the aircraft in comparison to ground level. For example, the third interior space sensor is based on a semiconducting metal oxide.

It is preferred that the outer space sensor device comprises a first outer space sensor which is adapted to measure the absolute pressure of the gases surrounding the outer space sensor, and/or a second outer space sensor which is adapted to measure the partial pressure of a gas surrounding the second outer space sensor, and/or a third outer space sensor which is adapted to measure the concentration of a gas surrounding the third outer space sensor, wherein preferably multiple first outer space sensors and/or multiple second outer space sensors and/or multiple third outer space sensors are provided.

In particular, the first outer space sensor is similar to the first interior space sensor, the second outer space sensor is similar to the second interior space sensor, and/or the third outer space sensor is similar to the third interior space sensor. By providing an outer space sensor device which corresponds to the interior space sensor device it is possible to determine the correlation of the absolute pressure, of the partial pressure, and/or of the concentration of a gas, which may reduce false positive alarms, as described above.

Providing multiple first interior space sensors, multiple first outer space sensors, multiple second interior space sensors, multiple second outer space sensors, multiple third interior space sensors, and/or multiple third outer space sensors may be used to localize the damage in the bonding. Differences in the measured concentration and/or of the measured pressures may indicate if the damage is located closer or farther from the individual sensors. This evaluation may take place by means of the control arrangement.

It is preferred that the interior space sensor device comprises different second interior space sensors and/or third interior space sensors which are adapted to measure the partial pressure and/or the concentration of different gases, respectively.

Providing different second interior space sensors and/or second outer space sensors which are adapted to measure the partial pressures of different gases, and/or providing different third interior space sensors and/or outer space sensors which are adapted to measure the concentration of different gases has the advantage that the false negative alarms may be reduced. If the partial pressure of different gases and/or the concentration of different gases changes by a certain value or correspondingly correlates with the partial pressure or with the concentration in the surroundings, this indicates that a damage in the bonding exists. Changes in concentration or in partial pressure of a gas may also be caused otherwise, so that this would be a false alarm in this case.

Alternatively or additionally, second and third interior space sensors and/or second and third outer space sensors may be provided for minimizing false negative alarms, which are adapted to measure the concentration or the partial pressure of different gases, respectively. For example, the second interior space sensor is adapted to measure the partial pressure of oxygen, while the third interior space sensor is adapted to measure the concentration of ozone.

It is preferred that the second interior space sensor is a coated optical fiber.

In particular, the optical fiber extends along a longitudinal direction of the first component element and/or of the second component element. Preferably, a duct is installed at the first component element and/or at a second component element, in which duct the optical fiber is guided. The duct is fluidically connected with the interior space, for example by providing openings in the duct. Providing a duct enables in a simple manner to insert or exchange the optical fiber, namely by inserting or taking out the optical fiber into or out of the duct.

The optical fiber may be provided with a corresponding coating or multiple coatings, by means of which the partial pressure of oxygen, in particular, may be determined. Providing an optical fiber for the second interior space sensor has the advantage that the partial pressure of oxygen can be locally determined by means of the optical fiber which may be used to determine the position of the damage in the bonding.

It is preferred that the component device is provided with a self-testing arrangement which is preferably adapted to heat or cool the interior space sensor device and/or the outer space sensor device.

In particular, the self-testing arrangement is in thermal contact with the interior space sensor device and/or with the outer space sensor device. In particular, for gas sensors which measure the concentration of a gas, as for example ozone or oxygen, the measured value changes depending on the temperature of the gas. Heating or cooling of the interior space sensor device and/or of the outer space sensor device, in particular of the third interior space sensor and/or of the third outer space sensor, may be used to generate a measured change in concentration of the gas. If the measured concentration of the gas changes as a result of heating or cooling this is an indication that the interior space sensor device and/or the outer space sensor device are functioning. For example, the self-testing arrangement may be provided in the form of a Peltier element or heating arrangement and, in particular, is connected to the control arrangement.

It is preferred that the component device is provided with a pressure compensation arrangement which is adapted to compensate pressure differences between the interior space and the surroundings of the component device, wherein preferably the pressure compensation arrangement comprises a gas reservoir which is arranged in the interior space and/or a counterbalance valve (precharging valve) which interconnects the interior space with the surroundings of the component device.

During flight of the aircraft at flight altitude, a very big pressure difference between the interior space and the surroundings may be generated due to temperature differences or due to big changes in pressure in the surroundings of the component device. In an extreme situation, this may result in damages at the first component element, the second component element, or the bonding.

As to avoid this, a gas reservoir may be provided in the interior space of the component device, which gas reservoir may compensate big changes in pressure, in particular changes above a certain threshold value. For this purpose, the gas reservoir is provided with a counterbalance valve which opens if the change in pressure in the interior space exceeds the threshold value.

Alternatively, a counterbalance valve may be provided directly in the first component element and/or in the second component element, so that it opens and provides for pressure compensation if the pressure difference between the interior space and the outer space exceeds the threshold value.

It is preferred that a membrane is provided at the component device, which membrane is adapted to be permeable for gases and impermeable for water vapor.

Preferably, the membrane is provided at one or both end faces of the first component element and the second component element. The membrane may be part of the closing device mentioned above and is adapted such that water vapor cannot penetrate through it while exchange of other gases is possible through the membrane. Hence, the membrane enables providing pressure compensation between the interior space and the outer space.

In particular, the second interior space sensor or the third interior space sensor is provided in connection with the membrane, which interior space sensors are adapted in this embodiment to determine the partial pressure of the water vapor or the concentration of the water vapor. As exchange of water vapor between the interior space and the outer space is not possible due to the membrane, change of the partial pressure of the water vapor or change of the concentration of the water vapor in the interior space indicates that a damage of the bonding exists.

Further, another aspect is directed to a method for detecting a damage of a bonding of a component device, in particular for a primary supporting component of an aircraft. The method comprises the steps: providing a component device which comprises two component elements being connected by the bonding and an interior space being fluidically connected to the bonding, which interior space is hermetically sealed for at least one type of gas, detecting the pressure and/or the concentration of the gas in the interior space, and determining a damage of the bonding if a change in pressure and/or in concentration above a predetermined threshold value is determined.

For example, the method may be executed by means of the component device as described above. Furthermore, the preferred embodiments, variants, and advantages depicted with reference to the component device apply in an analogous manner.

Moreover, the method may comprise the step: detecting the pressure and/or the concentration of the gas out of the component device and determining a damage of the bonding if the course of the pressure and/or of the concentration of the gas in the interior space and out of the interior space correlates.

It is preferred that the method further comprises the step: detecting the pressure and/or the concentration of different gases in the interior space, and determining a damage of the bonding if a change of the pressures above a predetermined threshold value is determined.

Moreover, the method may comprise the step: detecting the pressure and/or the concentration of the gas in the interior space at multiple positions and localizing the damage of the bonding by determining the pressure differences and/or concentration differences between the individual positions.

It is preferred that the method further comprises the step: monitoring the course of the pressure and/or of the concentration in the interior space over a predetermined period of time, and determining a damage of the bonding if a deviation of the course of the pressure from a predetermined course of the pressure is above a predetermined threshold value.

This step is especially suitable if the interior space permits a gas exchange with the surroundings up to a certain grade. In this case, changes in pressure and concentration in the interior space arise, for example during a flight of the aircraft. These may be recorded; for example, depending on the flight altitude. This recording may correspond to the predetermined course of pressure. In case of a damage in the bonding, the change in pressure and/or change in concentration varies, for example, a quicker approximation of the differences in pressure and/or concentration between the outer space and the interior space takes place as the damage provides an additional gas connection. This deviation from the predetermined course may be considered as evidence for a damage.

Further, another aspect relates to a method for detecting a damage of a bonding of a component device, in particular for a primary supporting component of an aircraft. The method comprises the steps: providing the component device which comprises two component elements being connected by the bonding and an interior space being fluidically connected to the bonding, which interior space is hermetically sealed for at least one type of gas, pumping this gas into the interior space, detecting the concentration of the gas out of the component device, and determining a damage of the bonding if the concentration if the gas is above a predetermined threshold value.

With regard to the component device at which the method is carried out, the considerations depicted above, the preferred embodiments, and advantages apply.

The interior space of this component device is hermetically sealed from the surroundings for at least one type of gas. This type of gas is now pumped into the interior space, so that the pressure of this gas increases there. Subsequently or at the same time, the concentration of this gas is determined outside the component device, in particular by means of the outer space sensor device described above, especially by means of the third outer space sensor. If the concentration of the gas in the surroundings of the component device increases above a predetermined threshold value, this indicates that a fluidical connection exists between the interior space and the surroundings, which in turn indicates that there is a damage in the bonding.

For example, the gas may be introduced into the interior space at the end faces of the first and second component element. Alternatively, a closable access may be provided in the first component element and/or in the second component element, by means of which closable access the gas can be introduced into the interior space.

"Pumping" shall be understood in this context such that the gas is introduced with pressure into the interior space. For example, the interior space may be connected to a gas container which is under pressure. In particular, it is possible to supply gas to the interior space continuously or interrupted in terms of time. For example, the gas is pumped into the interior space with pressure and the escaping (leaking) of the gas from the interior space is monitored by means of the outer space sensor arrangement. If the pressure of the gas in the interior space drops below a threshold value, gas may be automatically or manually re-pumped. For this purpose, the first component element and/or the second component element is preferably provided with a filling valve.

It is preferred that the outer space sensor device comprises a fluid detector which is adapted to detect the concentration of condensed gas.

If the component device is positioned in rooms which are very cold or the walls of which are very cold, there exists the possibility that the escaping gas condenses. This applies especially if the escaping gas has a condensation point which is close to or just above or below the temperature of the room. Due to the condensation, the concentration of the gas increases so that even very small concentrations of the escaping gas can be measured in the air. This applies especially if the gas is released to a small amount only and if the condensation of the escaping gas results in an accumulation of the concentration of the gas in terms of time.

This fluid detector may be arranged, for example, below or under a collection arrangement as, for example, a funnel, so that as much condensed marker gas as possible reaches the fluid detector. The fluid detector may be provided, for example, at a cold wall or at a cooled position of the first and/or second component element.

According to a further embodiment, the fluid detector may be integrated in existing draining elements of the aircraft.

It is preferred that the method further comprises the step of moving the outer space sensor device along the component device and determining the position of the damage of the bonding by monitoring the concentration of the gas.

For example, the outer space sensor device, in particular the third outer space sensor, may be provided as portable sensor which is moved along the first and/or second component element. An increase of the concentration of the gas during this movement indicates that the outer space sensor device is moved towards the damage in the bonding. If the concentration of the gas decreases, this indicates that the outer space sensor device moves away from the position of the damage of the bonding. In this manner, the position of the damage in the bonding may be determined. Furthermore, the extent of the concentration of the gas close to the position of the damage may be considered an indication of how much gas can escape from the interior space and, hence, of the extent of the damage in the bonding.

BRIEF DESCRIPTION OF THE DRAWINGS

The various embodiments will hereinafter be described in conjunction with the following drawing figures, wherein like numerals denote like elements, and.

DETAILED DESCRIPTION

The following detailed description is merely exemplary in nature and is not intended to limit the disclosed embodiments or the application and uses thereof. Furthermore, there is no intention to be bound by any theory presented in the preceding background detailed description.

Figure 1:
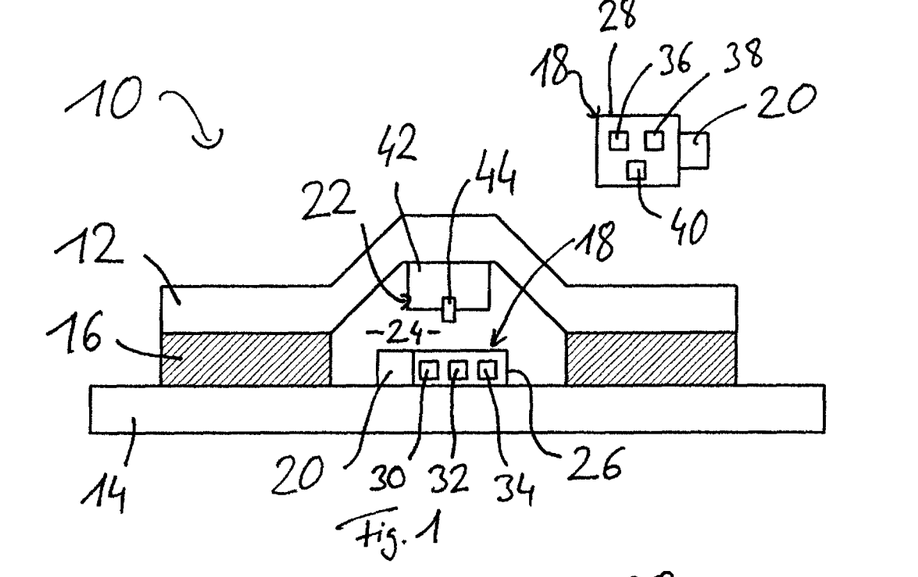
FIG. 1 is a cross section through a first embodiment of the component device without a damage in the bonding.
Figure 2:
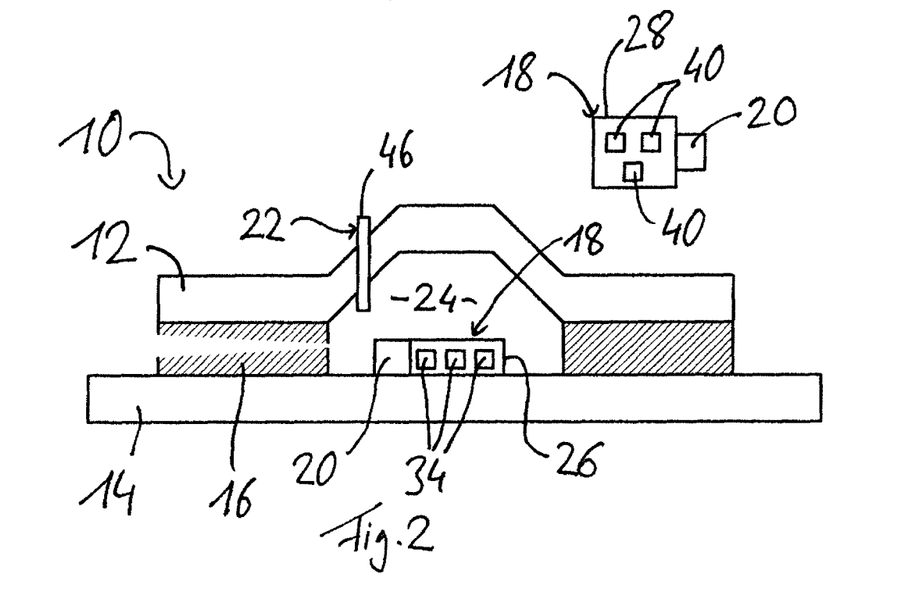
FIG. 2 is a cross section through a second embodiment of the component device with a damage in the bonding.
Figure 3:
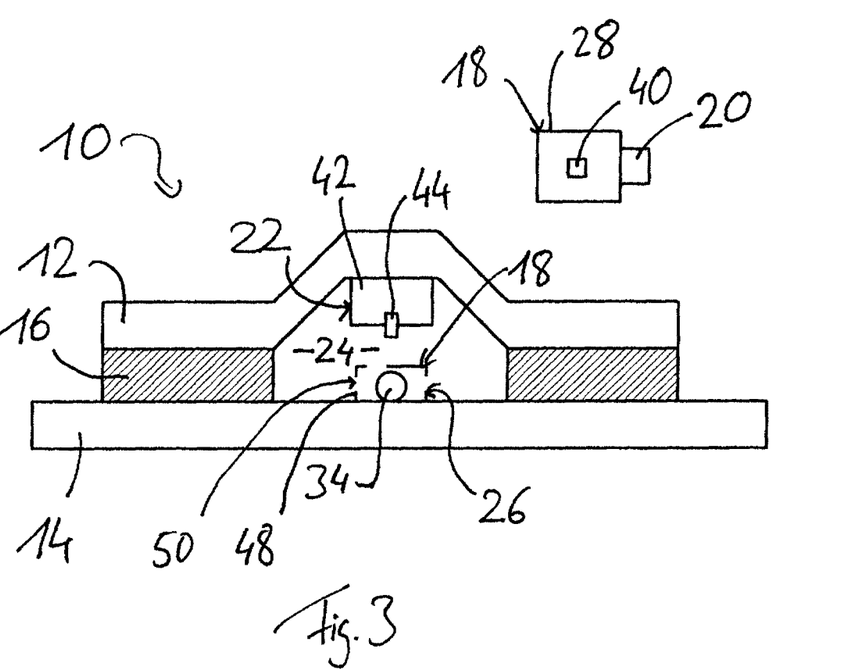
FIG. 3 is a cross section through a third embodiment of the component device without a damage in the bonding.

The component device 10 shown in the figures comprises a first component element 12, a second component element 14, a bonding 16, a detector device 18, a self-testing arrangement 20, and a pressure compensation arrangement 22.

The first component element 12 is an omega stringer made of a composite material. The second component element 14 is a part of an outer skin of an aircraft which is likewise made of a composite material. The first component element 12 is adhesively connected to the second component element 14 by the bonding 16. The bonding 16 is shown in FIGS. 1 to 3 in a magnified manner and is produced on the basis of resin.

An interior space 24 is created by the first component element 12, the second component element 14, and the bonding 16, wherein the end faces of the interior space are closed. Thus, the interior space 24 is hermetically sealed or sealed in a gas-tight manner from the surroundings of the first component element 12 and of the second component element 14, provided that the bonding 16 is without any damage.

The detector device 18 comprises an interior space sensor device 26 which is arranged in the interior space 24 mounted to the second component element 14—or in other embodiments which are not shown mounted to the first component element 12—, and an outer space sensor device 28. The interior space sensor device 26 and the outer space sensor device 28 are connected in a wireless manner with the control arrangement which is not shown in the figures. The control arrangement is the computer system of the aircraft.

The interior space sensor device 26 comprises a first interior space sensor 30, a second interior space sensor 32, and a third interior space sensor 34. Each of the interior space sensors 30, 32 is fluidically connected with the gas being present in the interior space 24. The first interior space sensor 30 is adapted to determine the absolute pressure of the gas in the interior space 24. The second interior space sensor 32 is adapted to determine the partial pressure of oxygen in the interior space 24, while the third interior space sensor 34 is adapted to determine the concentration of ozone in the interior space 24.

The outer space sensor device 28 is mounted to a wall of a room in which the first component element 12 and the second component element 14 are provided. The outer space sensor device 28 comprises a first outer space sensor 36, a second outer space sensor 38, and a third outer space sensor 40.

The first outer space sensor 36 is adapted to measure the absolute pressure of air in the surroundings of the first component element 12 and of the second component element 14. The second outer space sensor 38 is adapted to determine the partial pressure of oxygen in the air in its surroundings. The third outer space sensor 40 is adapted to determine the concentration of ozone in the surrounding air.

The self-testing arrangement 20 is in thermal contact with the interior space sensor device 26 and with the outer space sensor device 28. The self-testing arrangement 20 is designed as heating element and may heat the interior space sensor device 26 and the outer space sensor device 28. Moreover, the self-testing arrangement 20 is connected in a wireless manner with the control arrangement, wherein the control arrangement may control the self-testing arrangement 20.

The pressure compensation arrangement 22 in the embodiment shown in FIG. 1 comprises a gas reservoir 42 and a gas reservoir counterbalance valve 44. The gas reservoir 42 is mounted to the first component element 12. In the gas reservoir 42, gas is stored which has higher pressure compared to the gas pressure in the interior space 24. In case the pressure in the interior space 24 drops below a certain threshold value, the gas reservoir counterbalance valve 44 opens and gas from the reservoir 42 may escape into the interior space 24. In this manner, too much pressure difference between the interior space 24 and the outer space may be prevented.

The functioning of the component device 10 is now described in the following. In case the bonding 16 is intact, the interior space 24 is gas-tight or hermetically sealed from the surroundings. Thus, the pressures measured by the first interior space sensor 30 and the second interior space sensor 32 do not correlate with the changes in pressure measured by the first outer space sensor 36 and the second outer space sensor 38. Also, the concentration of ozone measured by the third interior space sensor 34 does not correlate with the changes in concentration of ozone which is measured by the third outer space sensor 40.

In case of a damage at the bonding 16, for example a crack in the bonding 16 as shown in FIG. 2, a gas connection exists between the interior space 24 and the surroundings. Hence, a correlation is now determined between the changes in pressure and changes in concentration of the gas between the interior space 24 and the surroundings by means of the interior space sensor device 26 and the outer space sensor device 28. In this case, the control arrangement provides a notification of an existing damage in the bonding 16.

False negative alarms may be reduced due to the fact that different gases are determined by the second interior space sensor 32 and the third interior space sensor 34. False positive alarms may be reduced by measuring the correlation between the interior space 24 and the outer space.

A second embodiment of the component device 10 is shown in FIG. 2. This is identical with the component device 10 of FIG. 1, except for the differences described in the following.

The interior space sensor device 26 comprises three third interior space sensors 34, each of which is adapted to determine the concentration of oxygen, ozone, and water vapor. Similarly, the outer space sensor device 28 comprises three third outer space sensors 40, each of which is adapted to determine the concentration of oxygen, ozone, and water vapor.

Moreover, the pressure compensation arrangement 22 in the embodiment shown in FIG. 2 is realized by a counterbalance valve 46. The counterbalance valve 46 is provided in the first component element 12 and establishes a connection between the interior space 24 and the surroundings if the pressure difference is above a certain threshold value. In this manner, high differences in pressure between the interior space 24 and the surroundings may be prevented, which high differences in pressure, in an extreme case, may cause damages at the first component element 12, the second component element 14, or the bonding 16.

The functioning of the component device 10 according to the embodiment shown in FIG. 2 is analogue to the embodiment according to FIG. 1.

In FIG. 3, a third embodiment of the component device 10 is depicted which is identical with the component device 10 according to FIG. 1, except for the following difference. The interior space sensor device 26 comprises a third interior space sensor 34 which is an optical fiber with a coating. The optical fiber serves for determining the ozone concentration in the interior space 24. The optical fiber is guided in a duct which is mounted to a second component element 14. Openings 50 are provided in the duct 48, which openings establish a connection between the interior of the duct 48 and the interior space 24 so that changes in concentration of the ozone in the interior space 24 may be determined by means of the optical fiber.

In the embodiment shown in FIG. 3, the outer space sensor device 28 comprises only one third outer space sensor 40 which is adapted to determine the concentration of ozone.

The functioning of the embodiment shown in FIG. 3 is similar to the functioning of the embodiment shown in FIGS. 1 and 2.

In a further variant, a damage in the bonding 16 may be determined in that gas is pumped into the interior space 24 and the changes in concentration of this gas in the surroundings is detected by means of the third outer space sensor 40. If the concentration of the gas changes in the outer space, this indicates that a damage exists in the bonding 16.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the embodiment in any way. Rather, the foregoing detailed description will provide those skilled in the art with a convenient road map for implementing an exemplary embodiment, it being understood that various changes may be made in the function and arrangement of elements described in an exemplary embodiment without departing from the scope of the embodiment as set forth in the appended claims and their legal equivalents.

LIST OF REFERENCE SIGNS 10 component device
12 first component element
14 second component element
16 bonding
18 detector device
20 self-testing arrangement
22 pressure compensation arrangement
24 interior space
26 interior space sensor device
28 outer space sensor device
30 first interior space sensor
32 second interior space sensor
34 third interior space sensor
36 first outer space sensor
38 second outer space sensor
40 third outer space sensor
42 gas reservoir
44 gas reservoir counterbalance valve
46 counterbalance valve 48 duct
50 opening

What is claimed is:

1. A component device for a primary supporting component of an aircraft, comprising:
   a first component element;
   a second component element;
   a bonding which provides a connection between the first component element and the second component element; and
   a detector device with at least one interior space sensor device that measures a change of the pressure and/or of a concentration of a gas surrounding the interior space sensor device;
   wherein the first component element, the second component element, and the bonding confine an interior space;
   wherein the interior space sensor device is arranged in the interior space;
   wherein the interior space sensor device comprises a first interior space sensor that measures the absolute pressure of the gases surrounding the first interior space sensor, a second interior space sensor that measures the partial pressure of a gas surrounding the second interior space sensor, and a third interior space sensor that measures the concentration of a gas surrounding the third interior space sensor; and
   wherein the interior space sensor device comprises a plurality of different second interior space sensors, each of which is configured to measure the partial pressure of a different gas, and/or a plurality of different third interior space sensors, each of which is configured to measure the concentration of a different gas.

2. The component device of claim 1, wherein the detector device comprises an outer space sensor device that measures the change of the pressure and/or of the concentration of a gas surrounding the outer space sensor device, and wherein the outer space sensor device is arranged outside of the interior space.

3. The component device of claim 1, further comprising a self-testing arrangement configured to heat or cool the interior space sensor device and/or the outer space sensor device.

4. The component device of claim 1, further comprising a pressure compensation arrangement that compensates pressure differences between the interior space and the surroundings of the component device, wherein the pressure compensation arrangement comprises a gas reservoir arranged in the interior space and/or a pressure relief valve interconnecting the interior space with the surroundings of the component device.

5. A component device for a primary supporting component of an aircraft, comprising:
   a first component element;
   a second component element;
   a bonding which provides a connection between the first component element and the second component element, wherein the first component element, the second component element, and the bonding confine an interior space;
   a detector device with at least one interior space sensor device that measures a change of the pressure and/or of a concentration of a gas surrounding the interior space sensor device, wherein the interior space sensor device is arranged in the interior space; and
   a pressure compensation arrangement that compensates pressure differences between the interior space and the surroundings of the component device, wherein the pressure compensation arrangement comprises a gas reservoir arranged in the interior space.

6. The component device of claim 5, wherein the second interior space sensor is a coated optical fiber.

7. A method for detecting a damage of a bonding for a component device, comprising the steps of:
   providing a component device comprising two component elements connected by the bonding and an interior space fluidically connected to the bonding, wherein the interior space is hermetically sealed for at least one type of gas;
   detecting the pressure and/or the concentration of the gas in the interior space;
   determining a damage of the bonding if a change in pressure and/or in concentration above a predetermined threshold value is determined,
   detecting the pressure and/or the concentration of the gas outside of the component device; and
   determining a damage of the bonding if time dependent measurements of the pressure and/or time dependent measurements of the concentration of the gas in the interior space and outside of the interior space correlates.

8. The method of claim 5, further comprising:
   monitoring time dependent measurements of the pressure and/or time dependent measurements of the concentration in the interior space over a predetermined period of time; and
   determining a damage of the bonding if a deviation of the time dependent measurements of the pressure from predetermined time dependent pressure measurements is above a predetermined threshold value.

9. A method for detecting a damage of a bonding for a component device, comprising the steps of:
   providing a component device comprising two component elements connected by the bonding and an interior space fluidically connected to the bonding, wherein the interior space is hermetically sealed for at least one type of gas;
   detecting the pressure and/or the concentration of the gas in the interior space;
   determining a damage of the bonding if a change in pressure and/or in concentration above a predetermined threshold value is determined;
   detecting the pressure and/or the concentration of additional gas in the interior space, the additional gas being different from the gas; and
   determining a damage of the bonding if a change of the pressures above a predetermined threshold value is determined.

10. A method for detecting a damage of a bonding for a component device, comprising the steps of:
    providing a component device comprising two component elements connected by the bonding and an interior space fluidically connected to the bonding, wherein the interior space is hermetically sealed for at least one type of gas;
    detecting the pressure and/or the concentration of the gas in the interior space;
    determining a damage of the bonding if a change in pressure and/or in concentration above a predetermined threshold value is determined;
    detecting the pressure and/or the concentration of the gas in the interior space at multiple positions; and localizing the damage of the bonding by determining the pressure differences and/or concentration differences between the individual positions.

\* \* \* \* \*